United States Patent
Harris

(10) Patent No.: US 9,005,218 B2
(45) Date of Patent: Apr. 14, 2015

(54) FOLLICULAR EXTRACTION METHOD AND DEVICE

(75) Inventor: James A. Harris, Denver, CO (US)

(73) Assignee: HSC Development LLC, Greenwood Village, CO (US)

( * ) Notice: Subject to any disclaimer, the term of this patent is extended or adjusted under 35 U.S.C. 154(b) by 1167 days.

(21) Appl. No.: 12/574,657

(22) Filed: Oct. 6, 2009

(65) Prior Publication Data

US 2010/0114118 A1    May 6, 2010

Related U.S. Application Data

(63) Continuation-in-part of application No. 11/102,550, filed on Apr. 8, 2005.

(60) Provisional application No. 60/560,397, filed on Apr. 8, 2004, provisional application No. 60/591,786, filed on Jul. 28, 2004.

(51) Int. Cl.
```
A61B 17/50      (2006.01)
A61B 17/3205    (2006.01)
A61B 17/34      (2006.01)
A61B 17/00      (2006.01)
A61B 17/32      (2006.01)
```

(52) U.S. Cl.
CPC ....... *A61B 17/32053* (2013.01); *A61B 17/3468* (2013.01); *A61B 2017/00752* (2013.01); *A61B 2017/320044* (2013.01)

(58) Field of Classification Search
USPC .......... 606/133, 131, 187, 184, 185, 190, 210
See application file for complete search history.

(56) References Cited

U.S. PATENT DOCUMENTS

| | | |
|---|---|---|
| 1,433,340 A | 10/1922 | Clark |
| 3,512,519 A | 5/1970 | Hall |
| 3,998,230 A | 12/1976 | Miller |
| 4,099,518 A | 7/1978 | Baylis et al. |
| 4,122,855 A | 10/1978 | Tezel |
| 4,160,453 A * | 7/1979 | Miller .......................... 606/187 |
| 4,476,864 A | 10/1984 | Tezel |
| 4,873,991 A | 10/1989 | Skinner |
| 5,019,091 A | 5/1991 | Porat et al. |

(Continued)

FOREIGN PATENT DOCUMENTS

| | | |
|---|---|---|
| EP | 1293167 A2 | 3/2003 |
| WO | 9947059 A1 | 9/1999 |

OTHER PUBLICATIONS

Korean Office Action issued on Apr. 27, 2009 in corresponding Korean Patent Application No. 10-2006-7022930 (English Translation attached).

(Continued)

*Primary Examiner* — Kathleen Holwerda
*Assistant Examiner* — Sarah Simpson
(74) *Attorney, Agent, or Firm* — Marsh Fischmann & Breyfogle LLP

(57) ABSTRACT

A method and device for the extraction of follicular units from a donor area on a patient. The method includes aligning a dissecting punch over a follicular unit and rotating the dissecting punch to score the epidermis layer of the skin so that hair follicles are disposed within the lumen. The dissecting punch is then moved through the dermis layer and fatty tissue layer of the skin to dissect the follicular unit from the tissue surrounding the follicular unit.

17 Claims, 11 Drawing Sheets

(56) References Cited

U.S. PATENT DOCUMENTS

| | | | |
|---|---|---|---|
| 5,036,860 A | 8/1991 | Leigh et al. | |
| 5,183,053 A | 2/1993 | Yeh et al. | |
| 5,269,316 A * | 12/1993 | Spitalny | 600/567 |
| 5,341,816 A | 8/1994 | Allen | |
| 5,417,683 A | 5/1995 | Shiao | |
| 5,439,475 A | 8/1995 | Bennett | |
| 5,507,765 A | 4/1996 | Mott | |
| 5,578,054 A | 11/1996 | Arnold | |
| 5,693,064 A | 12/1997 | Arnold | |
| 5,707,362 A | 1/1998 | Yoon | |
| 5,725,553 A | 3/1998 | Moenning | |
| 5,766,177 A | 6/1998 | Lucas-Dean et al. | |
| 5,782,851 A | 7/1998 | Rassman | |
| 5,792,163 A | 8/1998 | Hitzig | |
| 5,792,169 A | 8/1998 | Markman | |
| 5,817,120 A | 10/1998 | Rassman | |
| 5,827,199 A | 10/1998 | Alexander | |
| 5,857,981 A | 1/1999 | Bucalo et al. | |
| 5,885,226 A | 3/1999 | Rubinstein et al. | |
| 5,895,403 A | 4/1999 | Collinsworth | |
| 5,922,000 A | 7/1999 | Chodorow | |
| 5,989,273 A | 11/1999 | Arnold | |
| 6,080,175 A | 6/2000 | Hogendijk | |
| 6,228,039 B1 | 5/2001 | Binmoeller | |
| 6,315,737 B1 | 11/2001 | Skinner | |
| 6,416,484 B1 | 7/2002 | Miller et al. | |
| 6,461,369 B1 | 10/2002 | Kim | |
| 6,572,625 B1 | 6/2003 | Rassman | |
| 6,579,281 B2 | 6/2003 | Palmer et al. | |
| 6,616,683 B1 | 9/2003 | Toth et al. | |
| 6,641,564 B1 | 11/2003 | Kraus | |
| 7,156,856 B2 | 1/2007 | Feller | |
| 7,172,604 B2 * | 2/2007 | Cole | 606/131 |
| 8,016,844 B2 * | 9/2011 | Privitera et al. | 606/167 |
| 2003/0097144 A1 | 5/2003 | Lee | |
| 2004/0116942 A1 | 6/2004 | Feller | |
| 2004/0193203 A1 | 9/2004 | Pak et al. | |
| 2004/0220589 A1 | 11/2004 | Feller | |
| 2004/0230213 A1 * | 11/2004 | Wulfman et al. | 606/167 |
| 2005/0203545 A1 | 9/2005 | Cole | |
| 2005/0245952 A1 | 11/2005 | Feller | |
| 2006/0173476 A1 * | 8/2006 | Bradica et al. | 606/179 |

OTHER PUBLICATIONS

Rassman et al. Follicular Unit Extraction: Minimally Invasive Surgery for Flair Transplantation. American Society for Dermatologic Surgery, Inc. 2002. vol. 28. pp. 720-728.

Examination Report from European Patent Office dated Nov. 12, 2010 in corresponding European Patent Application No. EP 05 77 6621.

Supplementary European Search Report issued on Jun. 22, 2010 in related European Patent Application No. EP 05 77 6621.

Notice of Rejection dated Jun. 15, 2010 (with English translation) from related Japanese Patent Application No. 2007-507527.

Office Action mailed by US Patent Office for U.S. Appl. No. 11/565,553 by Cole (dated May 12, 2010).

Response to Office Action for U.S. Appl. No. 11/565,553 by Cole (dated Aug. 12, 2010).

* cited by examiner

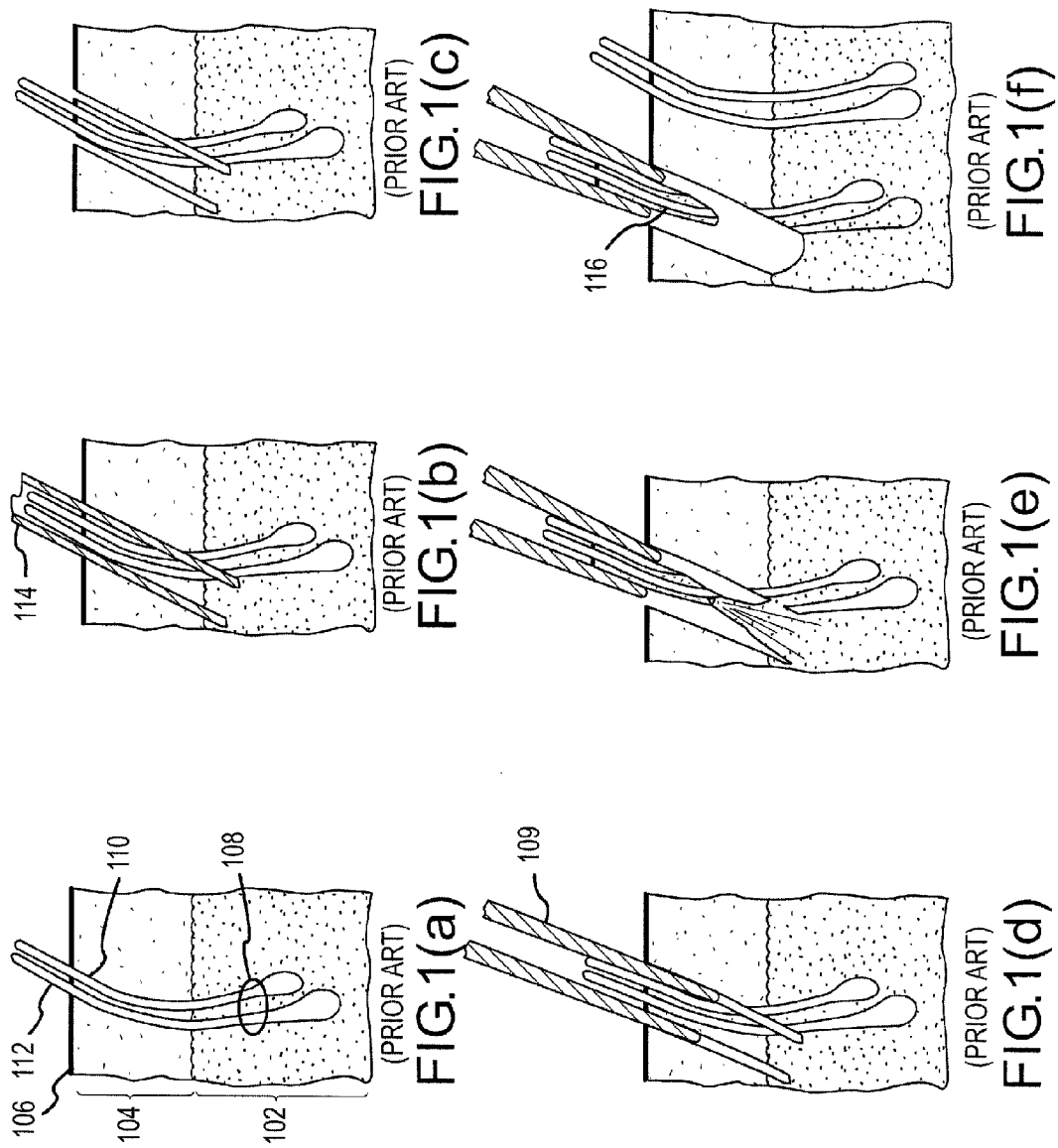

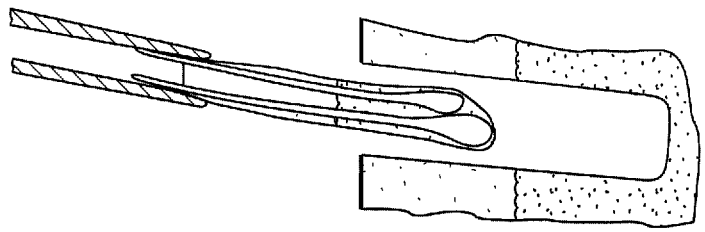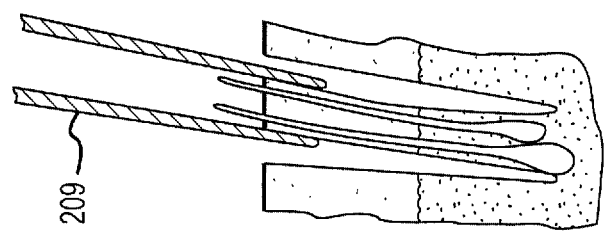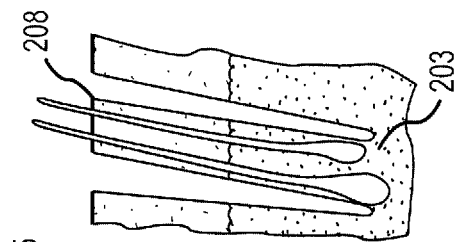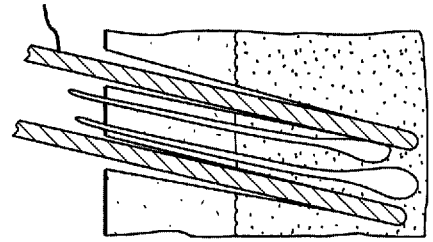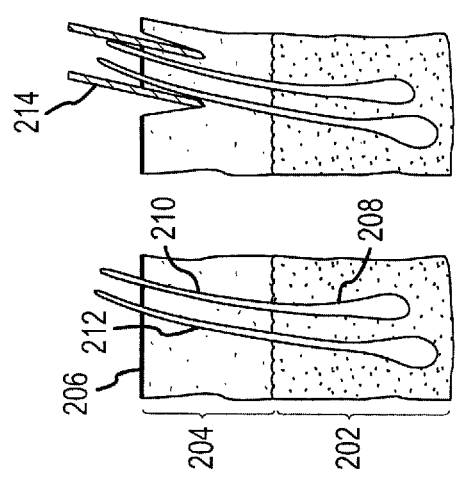
FIG.2(a) FIG.2(b) FIG.2(c) FIG.2(d) FIG.2(e) FIG.2(f)

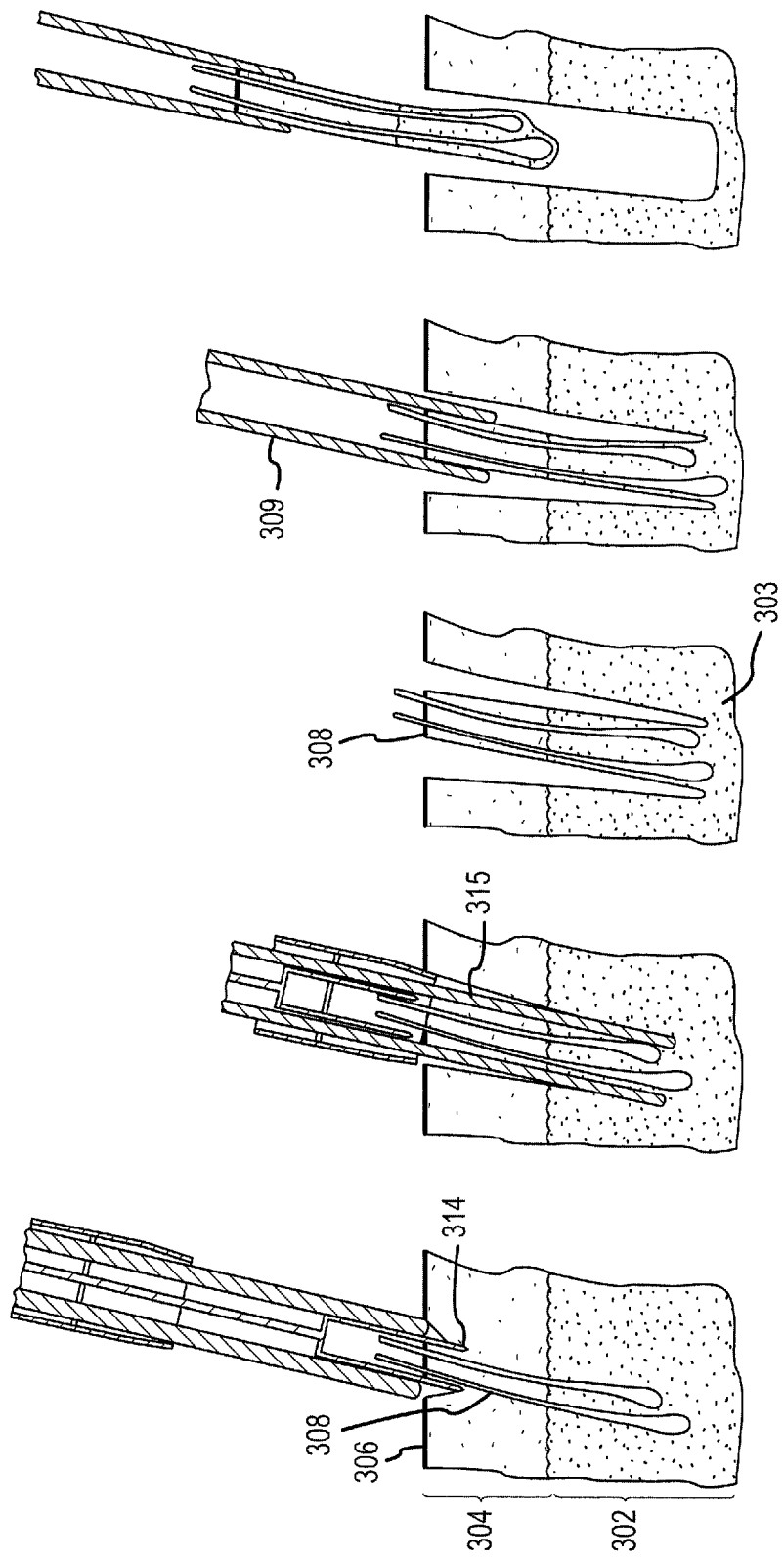

FOLLICULAR EXTRACTION METHOD AND DEVICE

CROSS-REFERENCE TO RELATED APPLICATIONS

This application is a continuation-in-part application of U.S. patent application Ser. No. 11/102,550, entitled FOLLICULAR EXTRACTION METHOD AND DEVICE filed on Apr. 8, 2005, which claims priority to U.S. Provisional Application Ser. No. 60/560,397 entitled FOLLICULAR EXTRACTION METHOD AND DEVICE, filed on Apr. 8, 2004, and U.S. Provisional Application Ser. No. 60/591,786 entitled FOLLICULAR EXTRACTION METHOD AND DEVICE, filed on Jul. 28, 2004. The disclosure of each of these applications is incorporated herein by reference in its entirety.

BACKGROUND OF THE INVENTION

1. Field of the Invention

The present invention relates to a method and device for the extraction of hair grafts from the donor area of a patient for subsequent transplantation to a recipient area. More specifically, the present invention relates to a method and device for the extraction of follicular hair units that decreases the follicular transection rate and improves the yield of transplantable follicular units.

2. Description of Related Art

The basic process of hair transplantation is to remove hair from the side and back fringe areas (donor areas) of the patient's head, and move it to the bald area (recipient area). Historically, 4 mm diameter plugs were utilized as the donor plug; this was followed by mini-grafts (smaller plugs), and finally by follicular units grafts (FUG's). FUG's are naturally occurring aggregates of 3-5 closely spaced hair follicles. The FUG's are distributed randomly over the surface of the scalp.

In the foregoing processes, a linear portion of the scalp is removed from the donor area by dissection with a scalpel. Some follicles are invariably transected during this process, damaging the follicles. In addition to some follicular damage, the removal of this donor strip will always result in a scar. In addition to the scar, there is usually a degree of moderate pain for several days and a sensation of tightness for 6-8 weeks following the procedure. Multiple procedures will result in multiple scars and thinning of the hair above and below the scar. If the pliability or laxity of the scalp is miscalculated, and a strip that is too wide is removed, this procedure has the potential to create a wide, unsightly scar because of the tension required to close the wound. Sometimes the resulting scar can be difficult to hide or disguise, causing a significant cosmetic deformity.

FUG's are dissected from a donor strip by several technicians using operating microscopes. Often the best technicians can produce approximately 250 to 300 grafts per hour, and an average technician produces closer to 200 grafts per hour. The FUG's are sorted into groups based upon the number of hairs contained in the FUG. The best technicians will have a transection rate of from about 2% to 5%.

Recently, Dr. William Rassman and Dr. Robert Bernstein disclosed a technique, called follicular unit extraction (FUE), whereby follicular units were extracted from the donor area without the need to create a linear incision with a scalpel. This was accomplished by using a sharp 1 mm diameter punch to make an incision into the epidermis and dermis, and then removing the follicular unit from the surrounding skin with forceps. Their findings suggested that some follicles were easily removed; others had a significant tendency to shear in the process. By their research, a good candidate was defined as one who experienced less than 20% shearing, and only about 25% of the patients tested were considered good candidates by their shearing test. This test is called the FOX (FOllicular eXtraction) test.

The foregoing procedure is technically difficult, as the penetration depth and penetration angle is difficult to control. If the sharp punch penetrates too deeply or at the incorrect angle there is a good chance of transecting the follicular unit. This method has not been widely adopted due to the problems of transection, difficulty removing the grafts, the time required to produce the grafts, and the low percentage of potential candidates Dr. John Cole, an expert in FUE, devised a device that limits the depth of the sharp punch to just below the attachment of the arrector pili muscle (presumably responsible for tethering the FUG to the deeper tissues and causing shearing during extraction), and increases the number of viable grafts produced. He has called his procedure the FIT, or Follicular Isolation Technique. He reports on his website that he has produced and transplanted up to 1200 grafts in one day. It is not believed that the time required to accomplish this has been more accurately reported.

The dissection of grafts from the scalps of African Americans and those with a high percentage of gray or white hairs is particularly problematic. The African American's follicles typically have a high degree of curl or curve, making the dissection difficult and prone to high transection rates. The follicles of white or gray hair are all but invisible, even under the microscope, making them prone to a high rate of transection as well.

There remains a need for a follicular extraction method and related device that reduces the amount of follicular transection and increases the follicular extraction rate.

BRIEF SUMMARY OF THE INVENTION

To address the problems associated with standard follicular unit production and the current FUE methodology, an improved method and device that may diminish or even eliminate the shortcomings of the existing technology is provided. The method and device may be used by the uninitiated operator with a degree of success similar to a trained individual.

The method generally may include rotating a blunt dissecting punch at a speed that is sufficiently high to enable an operator to score (cut) the epidermis layer of a patient's skin surrounding a follicular unit without applying undue pressure, despite the blunt (dull) nature of the dissecting punch. In this regard, the dissecting edge of the dissecting punch is relatively dull as compared to a sharp punch such as a standard biopsy punch, and at relatively low rotation speeds (e.g., as would be obtainable by manual hand rotation) would not be capable of easily scoring the epidermis layer of the patient's skin. However, by rotating the blunt dissecting punch at a sufficiently high speed, the dull dissecting edge may score the epidermis layer without undue pressure being applied to the dissecting punch.

Once the dissecting edge scores the epidermis layer of the patient's skin, the blunt dissecting punch is moved through the dermis layer and into the fatty tissue layer of the skin to dissect (separate) the follicular unit from the surrounding tissue. In this regard, the rotational speed of the blunt dissecting punch may be lowered to decrease the probability of transecting the follicular unit. That is, by lowering the rotational speed of the blunt dissecting punch, the cutting ability of the dissecting edge may be decreased, but is still sufficient to easily move the dissecting punch through the fatty tissue layer surrounding the follicular unit to dissect the follicular unit from the surrounding fatty tissue. Rather than cutting the follicular unit below the epidermis layer, the slowly rotating blunt dissecting punch will move the follicular unit into a lumen disposed within the dissecting punch. In this manner, accidental transection of the follicular unit may be avoided and the number of transected (damaged) follicular units extracted from a patient may be significantly reduced. The method may advantageously provide a rapid means to dissect and extract follicular units from a donor area with few damaged follicular units, even in high risk patients.

The method may be carried out using a drill having a blunt dissecting punch disposed at an end of the drill. The drill may be operated manually or in an automated fashion, and may include various controls for the rotational speed and/or torque of the rotating dissecting punch.

Thus, in one embodiment, a method for the extraction of a follicular unit from a donor area is provided. The method may include the steps of aligning a blunt dissecting punch over a follicular unit in a donor area and rotating the blunt dissecting punch at a first rotational speed. The blunt dissecting punch may include a lumen along an elongated axis of the punch and a dissecting edge disposed at a distal end of the lumen. The rotating blunt dissecting punch may be inserted through the epidermis layer of the skin to score the epidermis layer, whereby one or more hair follicles of a follicular unit are at least partially disposed within the lumen. The rotating blunt dissecting punch may then be moved through the dermis layer and into the fatty tissue layer of the skin, whereby at least a portion of the follicular unit is disposed within the lumen to bluntly dissect the follicular unit from the tissue surrounding the follicular unit. Thereafter, the dissected follicular unit may be extracted from the donor area.

A number of feature refinements and additional features may be separately applicable to the foregoing embodiment. These feature refinements and additional features may be implemented individually or in any combination. In one aspect, the dissecting edge may be substantially circular. For example, the circular dissecting edge may have an inner diameter of at least about 0.1 mm and not greater than about 1.1 mm, such as at least about 0.7 mm and not greater than about 1.1 mm. Such a size is particularly adapted for surrounding a single follicular unit without impinging upon an adjacent follicular unit. In another aspect, the blunt dissecting punch may be moved through the skin layers to a total depth of at least about 1.5 mm and not greater than about 8 mm, such as at least about 4 mm and not greater than about 7 mm. Such a depth is typically sufficient for separating the follicular unit from the surrounding fatty tissue layer to enable the follicular unit to be easily extracted from the patient's skin.

According to another aspect, the step of extracting the follicular unit from the donor area may include pulling the follicular unit from the donor area, such as by using forceps or tweezers to grip and pull the follicular unit after the blunt dissecting punch has separated the follicular unit from the surrounding tissue. After dissection using the blunt dissecting punch, the follicular unit will only be tenuously anchored at the very bottom of the follicular unit and may be easily removed by gently pulling on the follicular unit, or by other means such as by applying suction to the follicular unit.

The first rotational speed should be sufficiently high to rapidly and easily score the epidermis layer of the skin, despite the relatively dull nature of the dissection edge. According to one aspect, the first rotational speed may be at least about 3000 rpm, such as least about 3500 rpm. According to a further aspect, the rotational speed of the blunt dissecting punch may be decreased to a second rotational speed before or during the step of moving the rotating blunt dissecting punch through the dermis layer and into the fatty tissue layer. The second rotational speed should be sufficiently low such that the probability of transecting the follicular unit with the dissecting edge is low. For example, the second rotational speed may be not greater than about 70 percent of the first rotational speed, such as not greater than about 50 percent of the first rotational speed. In one aspect, the second rotational speed may be not greater than about 2000 rpm, such as not greater than about 1500 rpm.

The rotational speed of the dissecting punch may be decreased manually or through a self-regulating mechanism. In one aspect, the step of rotating the blunt dissecting punch may include rotating the blunt dissecting punch at a torque that is sufficiently low such that the friction between the blunt dissecting punch and the skin layers causes the rotational speed of the blunt dissecting punch to decrease to the second rotational speed, such as not greater than about 60 percent of the first rotational speed. That is, the rotational speed of the blunt dissecting punch may decrease in a self-regulated manner due to friction encountered as the punch moves into the skin layers, if the torque of the rotating dissecting punch is sufficiently low. In one aspect, the second rotational speed may be not greater than about 50 percent of the first rotational speed. In another aspect, the torque of the rotating dissecting punch is not greater than about 0.3 N·m.

According to another embodiment, a method for the extraction of a follicular unit from a donor area is provided. The method may include the steps of aligning a blunt dissecting punch over a follicular unit in a donor area and rotating the blunt dissecting punch at a first rotational speed, such as at least about 2500 rpm. The blunt dissecting punch may include a lumen along an elongated axis of the punch and a circular blunt dissecting edge disposed at a distal end of the lumen, where the circular blunt dissecting edge has an inner diameter of at least about 0.7 mm and not greater than about 1.1 mm. The rotating blunt dissecting punch may be inserted through the epidermis layer of the skin to score the skin, whereby one or more hair follicles of a follicular unit are at least partially disposed within the lumen. The rotating blunt dissecting punch may be moved through the dermis layer and into the fatty tissue layer of the skin, whereby at least a portion of the follicular unit is disposed within the lumen to bluntly dissect the follicular unit from tissue surrounding the follicular unit. In this regard, the rotational speed of the blunt dissecting punch may be decreased to a second rotational speed that is not greater than about 70 percent of the first rotational speed when the blunt dissecting punch is moved through the dermis layer and into the fatty tissue layer. Thereafter, the follicular unit may be removed from the donor area such as by pulling the follicular unit with forceps.

A number of feature refinements and additional features may be separately applicable to the foregoing embodiment. These feature refinements and additional features may be implemented individually or in any combination. For example, in one aspect, the step of rotating the blunt dissecting punch may include rotating the blunt dissecting punch at a torque that is sufficiently low such that the friction between the blunt dissecting punch and the skin layers causes the rotational speed of the blunt dissecting punch to decrease to the second rotational speed. According to another aspect, the second rotational speed is not greater than about 1000 rpm. In another aspect, the rotational speed of the blunt dissecting punch may be decreased manually.

According to another embodiment, a device that is adapted for the dissection of a follicular unit from a donor area is provided. The device may include a blunt dissecting punch and a rotation mechanism for rotating the blunt dissecting punch. The blunt dissecting punch may include a lumen along its elongated axis and a circular blunt dissecting edge disposed at a distal end of the lumen. The circular blunt dissecting edge may have an inner diameter, for example, of at least about 0.1 mm and not greater than about 1.1 mm.

A number of feature refinements and additional features may be separately applicable to the foregoing embodiment. These feature refinements and additional features may be implemented individually or in any combination. For example, in one aspect, the rotation mechanism may be adapted for rotating the blunt dissecting punch at a rotational speed of at least about 3000 rpm, such as at least about 3500 rpm. In another aspect, the circular blunt dissecting edge may have an inner diameter of at least about 0.7 mm. According to another aspect, the lumen may have a length of at least about 8 mm. According to a further aspect, the blunt dissecting punch may include a dissecting tip at a distal end of the dissection punch, where the tip may be tapered inwardly toward the dissecting edge to ease insertion of the blunt dissecting punch into the skin. According to a further aspect, the device may include a depth-limiting mechanism that is adapted to limit the depth of insertion of the blunt dissecting punch into the skin. The depth-limiting mechanism may be adapted to limit the depth of insertion of the blunt dissecting punch to not greater than about 5 mm. For example, the depth-limiting mechanism may include a shoulder that is disposed on the blunt dissecting punch above a dissecting tip that is at a distal end of the blunt dissecting punch. Such a depth-limiting mechanism may enable an operator to move the dissecting punch through the skin layers without concern for penetrating the skin too deeply.

According to another aspect, the rotation mechanism may include a motor that is operatively coupled to the blunt dissecting punch. For example, the motor may be adapted to rotate the blunt dissecting punch at a rotational speed of at least about 3500 rpm. In another aspect, the rotation mechanism may be adapted to rotate the blunt dissecting punch at a torque that is sufficiently low such that during insertion of the blunt dissecting punch into the skin, friction between the blunt dissecting punch and the skin layers causes the initial rotational speed of the blunt dissecting punch to decrease to a speed that is not greater than about 70 percent of the initial rotational speed. For example, in one aspect the rotation mechanism is adapted to rotate the blunt dissecting punch at a torque that is at least about 0.01 N·m and is not greater than about 0.04 N·m.

According to another aspect, the device may include a drill body that is adapted to be gripped by a user to position the blunt dissecting punch over a follicular unit. In another aspect, the circular dissecting edge may be serrated. According to another aspect, the blunt dissecting punch may be removable form the rotation mechanism. In this manner, the blunt dissecting punch may be removed and autoclaved for subsequent use. For example, the blunt dissecting punch may be operatively coupled to the rotation mechanism using a chuck or a similar clamping device. In another aspect, the rotational speed of the blunt dissecting punch may be manually adjusted. In yet another aspect, the torque of the rotating blunt dissecting punch may be manually adjusted.

The method and device according to the present invention can provide value to both the patient and physician. Some of the benefits may include one or more of the following:

Patient Benefits
  Reduce follicular transection, thus extracting more hair to transplant
  Increase donor capability by 50% to 80% (no longer limited by scalp laxity)
  Decrease post-operative pain
  Speed healing
  No visible scarring
  Possible faster graft growth
  African American and gray haired patients will benefit significantly from less follicle damage Physician Benefits
  Decrease follicular transection
  More exact planning for the number of grafts required
  Ability to select certain FUG's (i.e., more 4 hair FUG's than 2 hair FUG's to create density or more 1 hair FUG's for the visible hairline)
  Decrease number of staff (FUG's can be obtained by physician alone, or by minimal number of qualified staff after limited training)
  The ability to obtain grafts from African American and gray haired patients with confidence and minimal transection
  The possibility of decreasing overhead and need for technical equipment (e.g., microscopes for graft dissection)
  The possibility of decreasing the price per graft and enlarge the potential market
  Marketing advantages to physicians offering superior patient outcomes from advanced technology and instrumentation These and other advantages of the present invention will become apparent to those of ordinary skill in the art upon consideration of the following description of the invention.

BRIEF DESCRIPTION OF THE DRAWINGS

FIG. 1 illustrates a follicular extraction method according to the prior art.

FIG. 2 illustrates a follicular extraction method according to an embodiment of the present invention.

FIG. 3 illustrates a follicular extraction device and method according to an embodiment of the present invention.

DESCRIPTION OF THE INVENTION

Figures 4A, 4B, 4C:
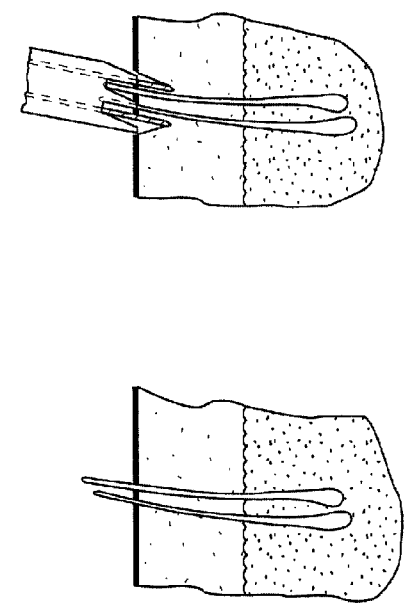
FIG. 4 illustrates a follicular extraction device and method according to an embodiment of the present invention.
Figure 4D:
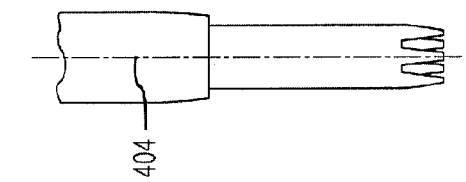
Figure 4E:
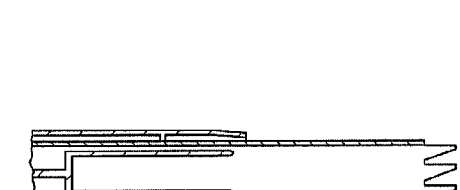
Figure 4F:
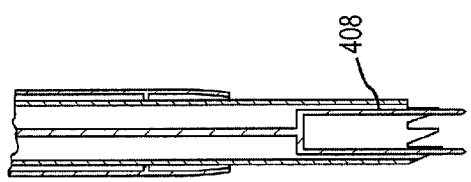
Figure 4G:
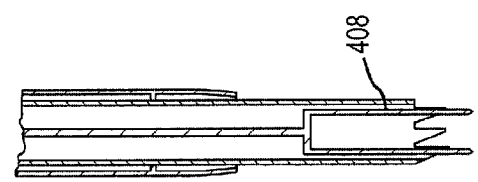

FIG. 1 schematically illustrates a follicular extraction technique according to the prior art, as developed by Dr. William Rassman and Dr. Robert Bernstein. See, for example, Rassman et al., *Dermatologic Surgery* 2002; 28:720-728. Referring to FIG. 1(a), the patient's skin includes a fatty layer 102, a dermis layer 104, and an epidermis layer 106. Within a donor area, a follicular unit 108 consisting of two hair follicles 110 and 112 extends through the dermis 104 and epidermis 106 layers and is anchored in the fatty layer 102. It will be appreciated by those skilled in the art that follicular unit can include more or less than two hair follicles.

During this follicular extraction technique, the operator aligns a sharp punch 114 substantially parallel with the protruding hairs, and the punch 114 is pushed into the skin with sufficient force such that the sharp edge of the punch 114 extends downwardly through the epidermis 106 and dermis 104 layers (FIG. 1(b). However, as is illustrated in FIG. 1(c), the hair follicles 110 and 112 are transected by the punch 114 if the hair follicles are not substantially parallel through the layers. The operator then removes the follicular unit 116 (FIGS. 1(d), 1(e), and 1(f)) using forceps 109 or a similar device. However, the removed follicular unit 116 is severed and is not useful for transplantation (FIG. 1(f)).

FIG. 2 illustrates a follicular extraction method according to one embodiment of the present invention. Generally, the method illustrated in FIG. 2 includes a two-step technique for the preparation of the follicular unit for extraction. The first step scores the skin surrounding the follicular unit and the second step separates the follicular unit from the surrounding tissue and fat in the form of a follicular unit plug without shearing the hair follicles.

Referring to FIG. 2(a), the patient's skin includes a fatty layer 202, dermis 204, epidermis 206, and a follicular unit 208. The follicular unit consists of two hair follicles, 210 and 212, extending through the dermis and epidermis, and anchored in the fatty layer 202.

The method illustrated in FIG. 2 includes the use of a sharp scoring punch 214 (FIG. 2(b)). The sharp scoring punch 214 includes a dissecting edge that is preferably circular in cross-section and preferably has an inner diameter of at least about 0.1 mm and not greater than about 1.1 mm. According to one embodiment, the dissecting edge of the scoring punch 214 has an inner diameter of from about 0.7 mm to about 1.0 mm. The dissecting edge of the scoring punch has a sufficient sharpness to cut through the epidermis 206, dermis 204 and fatty layer 202 with relative ease, as is known to those skilled in the art. An example is the 1 mm Dermal Biopsy Punch available from Miltex, Inc., Bethpage, N.Y.

The operator aligns the sharp scoring punch 214 approximately parallel to the hairs 210 and 212 protruding from the epidermis 206 with the protruding hairs being disposed within the lumen of the scoring punch 214. The operator then applies a limited amount of force to the scoring punch 214 such that the scoring punch cuts through the epidermis 206 and scores (partially cuts through) the upper dermis 204, preferably to a total depth of not greater than about 1.5 mm, such as from about 0.3 mm to about 1.5 mm. The sharp scoring punch 214 should be inserted to a depth sufficient to score the skin and upper dermis but not so deep as to risk transection of the follicles. The sharp scoring punch 214 is then removed.

As is illustrated by FIG. 2(c), a blunt dissecting punch 215 that is less sharp than the scoring punch is then placed into the scored incision created by the scoring punch 214. The blunt dissecting punch 215 has an inner diameter that is fractionally larger than the outer diameter of the scoring punch 214, whereby the dissecting punch 215 can readily advance through the incision created by the scoring punch 214. The blunt dissecting punch 215 is less sharp than the scoring punch 214, and the leading edge of the dissecting punch 215 is such that the probability of shearing a hair follicle (e.g., hair follicle 210) is very low. However, the dissecting punch 215 is capable of advancing through the softer dermis 204 and fatty layer 202 without overdue pressure being applied by the operator.

The dissecting punch 215 is advanced through the dermis 204 and the fatty layer 202 to a depth that is sufficient to enable the subsequent removal of the follicular unit 208 in the form of a follicular unit plug (i.e., the follicular unit and immediate surrounding tissue) without substantially damaging the follicular unit 208. Accordingly, the dissecting punch 215 penetrates to a depth that is deeper than the insertion depth of the scoring punch 214 and can be fully inserted through the dermis layer 204 and into the fatty layer 202. According to one embodiment, the dissecting punch 215 is inserted to a total depth of at least about 1.5 mm and not greater than about 8 mm, such as from about 4 mm to about 7 mm (FIG. 2(c)). In one embodiment, the dissecting punch 215 is inserted to a depth of not greater than about 5 mm. This bluntly separates the fibrous attachments surrounding the follicular unit 208, leaving it attached only at its base 203 (FIG. 2(d)). The surgeon then removes the follicular unit 208 from the skin using forceps 209, or a similar device. The follicular unit 208 is removed intact and is ready for implantation at a recipient site.

It will be appreciated by those of ordinary skill in the art that the scoring punch 214 and the dissecting punch 215 can be fabricated from materials normally used for such purposes, such as rigid or semi-rigid materials and the like, particularly metals. It is preferred that the cross-section of each of the scoring punch and the dissecting punch is circular for a variety of reasons, including that a circular cross-section enables the operator to twist (rotate) the punch to facilitate movement into and through the various skin layers. However, other cross-sections may be useful, such as the elliptical biopsy punch disclosed by Yeh et al. in U.S. Pat. No. 5,183,053, which is incorporated herein by reference in its entirety.

It will be appreciated that the method illustrated in FIG. 2 can be carried out utilizing two or more separate devices for the scoring step and the dissecting step. That is, a first device having a sharp punch and a second device having a blunt punch can be used to dissect and extract the follicular unit.

However, in a preferred embodiment, the method of FIG. 2 is carried out using a single device that incorporates both the sharp scoring punch and the blunt dissecting punch. For example, the device can include a sharp punch disposed at one end of a rigid handle and a dissecting blunt punch at the other end of the handle.

FIG. 3 illustrates such a device according to one embodiment of the present invention. The device includes a sharp scoring punch 314 for scoring the skin layers, as is described above. The sharp scoring punch 314 can have an outer diameter as is described with respect to FIG. 2, and in one embodiment has an outer diameter of about 1 mm.

Figure 5:
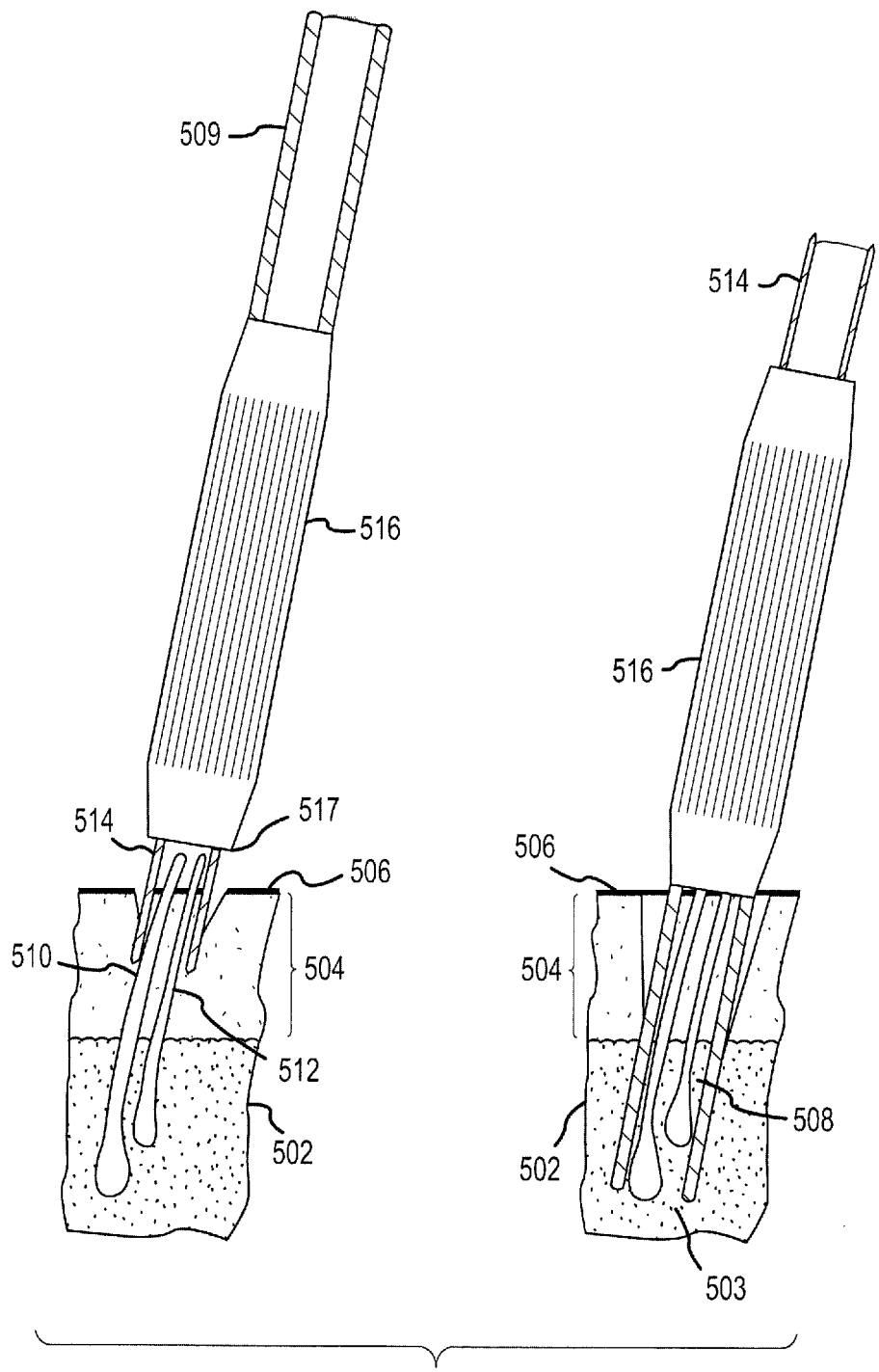
FIG. 5 illustrates a follicular extraction device and method according to an embodiment of the present invention.

In the embodiment illustrated in FIG. 3, the sharp scoring punch 314 is disposed within the lumen of an outer blunt dissecting punch 315. The operator aligns the device, specifically the scoring punch 314, approximately parallel to the hairs 310 and 312 protruding from the epidermis, such that the protruding hairs 310 and 312 are disposed within the lumen of the sharp scoring punch 314. The device, with the sharp scoring punch 314 extended, sharply cuts through the epidermis 306 and scores the upper dermis 304, preferably to a total depth of not greater than about 1.5 mm, such as from about 0.3 mm to about 1.5 mm, the depth of the incision preferably being limited by the device (FIG. 3(a)). As is illustrated in FIG. 3, the incision depth of the scoring punch 314 is limited by the end of the dissecting punch 315. The sharp scoring punch 314 is then retracted into the lumen of the dissecting punch 315, and the dissecting punch 315 is advanced into the score created by the scoring punch and through the dermis 304 and into the fatty layer 302, preferably to a depth as discussed above with respect to FIG. 2, such as from about 4 mm to about 7 mm (FIG. 3(b)). The insertion depth of the dissecting punch is also preferably limited to the preferred depths disclosed herein by the device. As is illustrated in FIG. 3(b), the insertion depth of the dissecting punch is limited by the end of the housing enclosing the scoring punch 314 and dissecting punch 315. The housing can also serve as the handle of the device to be gripped by the operator, as is illustrated in the embodiment of FIG. 5.

The action of the dissecting punch 315 bluntly separates the fibrous attachments surrounding the follicular unit 308, leaving it attached only at its base 303 (FIG. 3(c)). The operator then removes the follicular unit 308 from the skin using forceps 309, or a similar device (FIGS. 3(d) and 3(e)), such as a tension device or a suction device, for example. The follicular unit is then ready for implantation at the recipient site.

FIG. 4 illustrates one embodiment of the present invention where the dissecting punch utilizes a serrated or "saw tooth" tip 401 comprising a plurality of splines. This modification allows the dissecting punch to more readily separate the attachments of the dermis to the follicular unit and allow advancement through the tissues with greater ease by using rotation, either manual rotation or automated rotation. Any number of splines 402 can be utilized and in one embodiment, the dissecting punch tip includes from 2 to 5 splines. One edge of the splines may be at an angle relative to the primary axis 404 of the dissecting punch, as illustrated in FIGS. 4(b), 4(c), 4(d), 4(e) and 4(f), or straight (substantially parallel to the primary axis 404 of the dissecting punch) as illustrated in FIG. 4(g). FIG. 4(d) shows the external appearance of the dissecting punch while FIGS. 4(e) and 4(g) represent a cross section of this modified dissecting punch tip showing a scoring punch 408 extended and retracted respectively.

It should also be noted that according to one embodiment the scoring punch and dissecting punch could be one in the same. More specifically, a single punch can include a number of splines that have a sharp leading edge and are capable of scoring the skin when rotated in one direction, and having a blunt trailing edge that is capable of dissecting without transecting the hair follicles when the punch is rotated in the opposite direction.

According to one embodiment, either a suction probe within the lumen of the device or mechanical forceps provide traction on the follicular unit in order to remove the follicular unit. Further, the device can include a mechanism for rotating the sharp scoring punch and/or dissecting punch as they are pressed into the patient's skin. Another embodiment includes a mechanism whereby a blade or biting scoop or dissecting wire is incorporated into the tip of the dissecting punch, and when activated will sever the fatty attachment at the base of the follicular unit to enhance the ease of plug removal from the surrounding skin. This modification may or may not include a method to remove the follicular unit in its entirety through the lumen of the device using mechanical grasping or suction application to the follicular unit, such as to move the follicular unit to a chilled holding solution.

FIG. 5 illustrates a follicular extraction device according to another embodiment of the present invention. The device includes a rigid handle 516, preferably made of medical grade plastic or other suitable material that can have a scored surface to promote the ease of handling. At one end, the device includes a sharp scoring punch 514 shown in cross-section for scoring the skin layers, as is described above. The sharp scoring punch 514 can have an outer diameter as is described with respect to FIG. 2, and in one embodiment has an outer diameter of approximately 1 mm. A blunt dissecting punch 509, shown in cross-section, is provided at the other end of the device and preferably has an inner diameter of from about 0.8 mm to about 1.0 mm. The leading edge of the dissecting punch 509 is less sharp than the scoring punch 514 so that the probability of shearing a hair follicle is very low.

The user can align the device, specifically the scoring punch 514, approximately parallel to the hairs 510 and 512 protruding from the epidermis such that the protruding hairs are disposed within the lumen of the sharp scoring punch 514. The device, held between the fingers, is rotated about the axis of the handle and sharply cuts through the epidermis 506 and scores the upper dermis 504, preferably to a total depth of from about 0.3 mm to about 1.5 mm, the depth of the incision preferably being limited by the device. In the embodiment illustrated in FIG. 5, the depth is limited by a lower surface 517 of the handle 516. The device is then rotated or "twirled" between the operator's fingers so that the dissecting punch 509 is in position over the protruding hairs 510 and the incised epidermis 506 and dermis 504. The dissecting punch is then advanced through the dermis 504 and the fatty layer 502, preferably to a depth as discussed above with respect to FIG. 2, such as from about 4 mm to about 7 mm, the depth preferably being limited by the device. This action bluntly separates the fibrous attachments surrounding the follicular unit 508, leaving it attached only at its base 503. The tip of the dissecting punch can also be serrated, as is described above and is illustrated in FIG. 4(f) and FIG. 4(g).

The operator can then remove the follicular unit 508 from the skin using forceps 509, or a similar device. The follicular unit is then ready for implantation at the recipient site. The process can be repeated multiple times to affect the proper number of follicular unit extractions.

Figure 6:
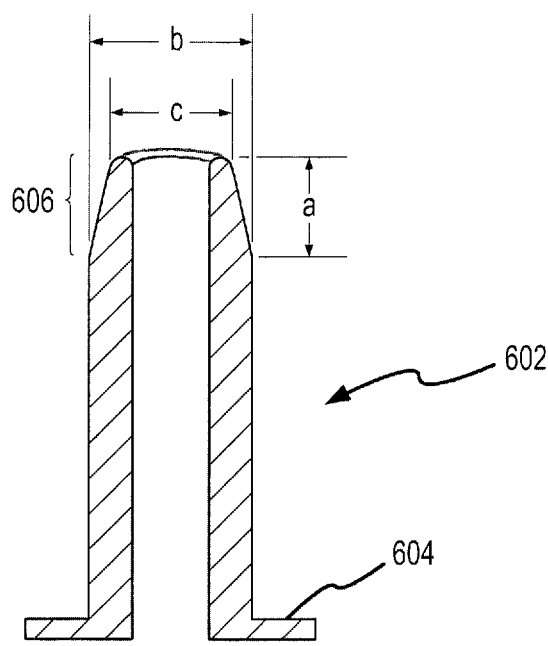
FIG. 6 illustrates the dissecting punch of a follicular extraction device according to an embodiment of the present invention.

According to one preferred embodiment of the present invention, the dissecting punch is tapered (e.g., beveled) to ease insertion of the punch into the scored skin. A cross-section of such a dissecting punch is illustrated in FIG. 6. The punch 600 includes a blunt dissecting tip 602 and a shoulder 604 adapted to restrict the penetration depth of the punch. The punch includes a tapered portion 606 to ease insertion of the punch and to enhance the separation of the follicular unit from the surrounding skin tissue. It will be appreciated that a taper can be applied to a non-serrated punch as well as a serrated punch. According to one embodiment, the length of the tapered portion (a) is at least about 0.3 mm and is not greater than about 0.7 mm. According to a more preferred embodiment, the tapered portion has a length of at least about 0.4 mm and not greater than 0.6 mm, such as about 0.5 mm. For efficient dissection, the tapered portion 606 preferably reduces the primary outside diameter by at least about 10% and not greater than about 30%, such as by about 20%. For example, in one embodiment the punch 600 has a primary outer diameter (b) of about 1.52 mm and a tip diameter (c) of about 1.24 mm, where the total length of the dissecting punch (e.g., to the shoulder 604) is about 5 mm and the inner diameter is about 1 mm.

Figure 7:
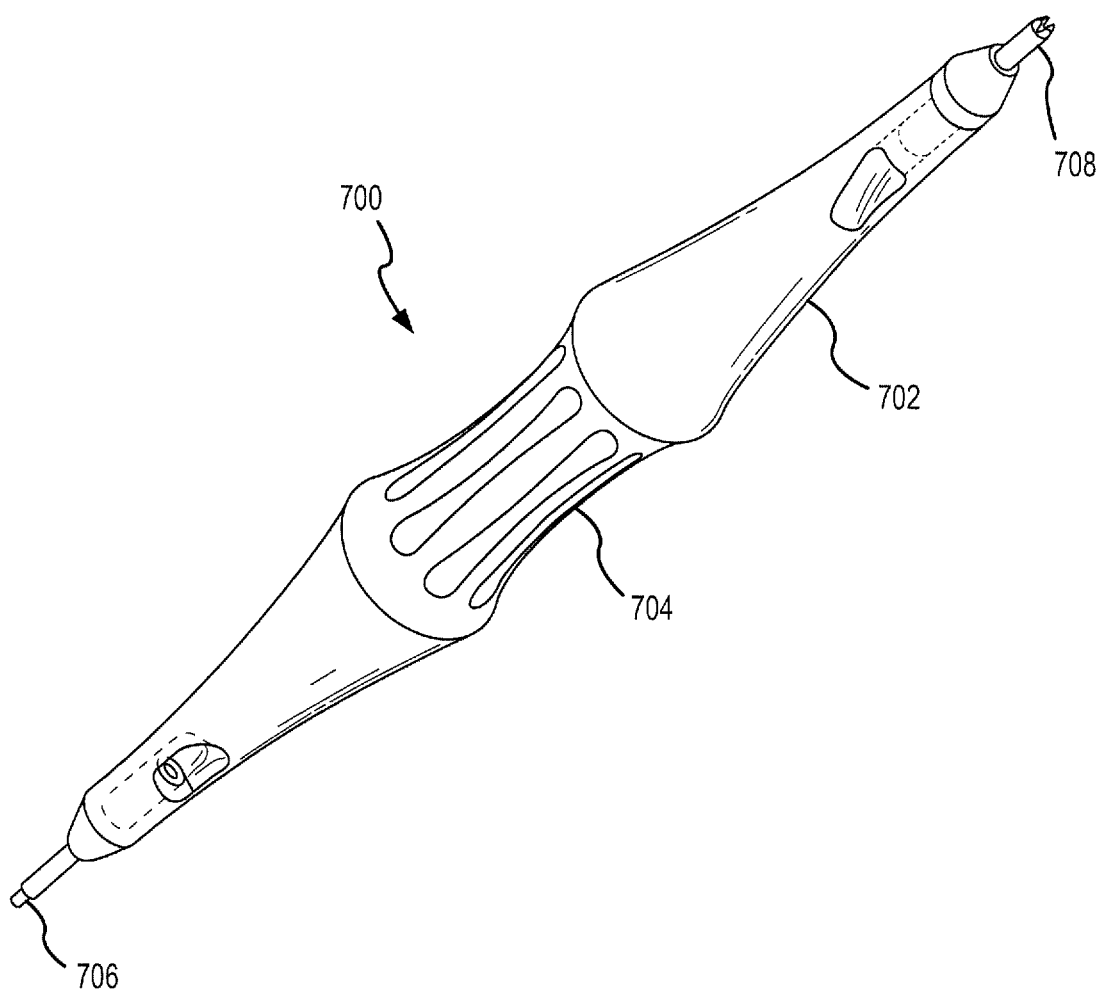
FIG. 7 illustrates a perspective view of a follicular extraction device according to an embodiment of the present invention.

FIG. 7 illustrates a perspective view of a follicular extraction device 700 according to another embodiment of the present invention. The device 700 includes an elongated handle 702 having a recessed mid-section 704 adapted to be gripped by a user. A first end of the handle 702 comprises a sharp scoring punch 706 adapted to score the epidermis and dermis of the patient. The device can then be flipped in the operator's hands and the blunt dissecting punch 708 located at a second end of the handle 702 can be used to dissect the follicular unit from the surrounding skin tissue.

Figure 8:
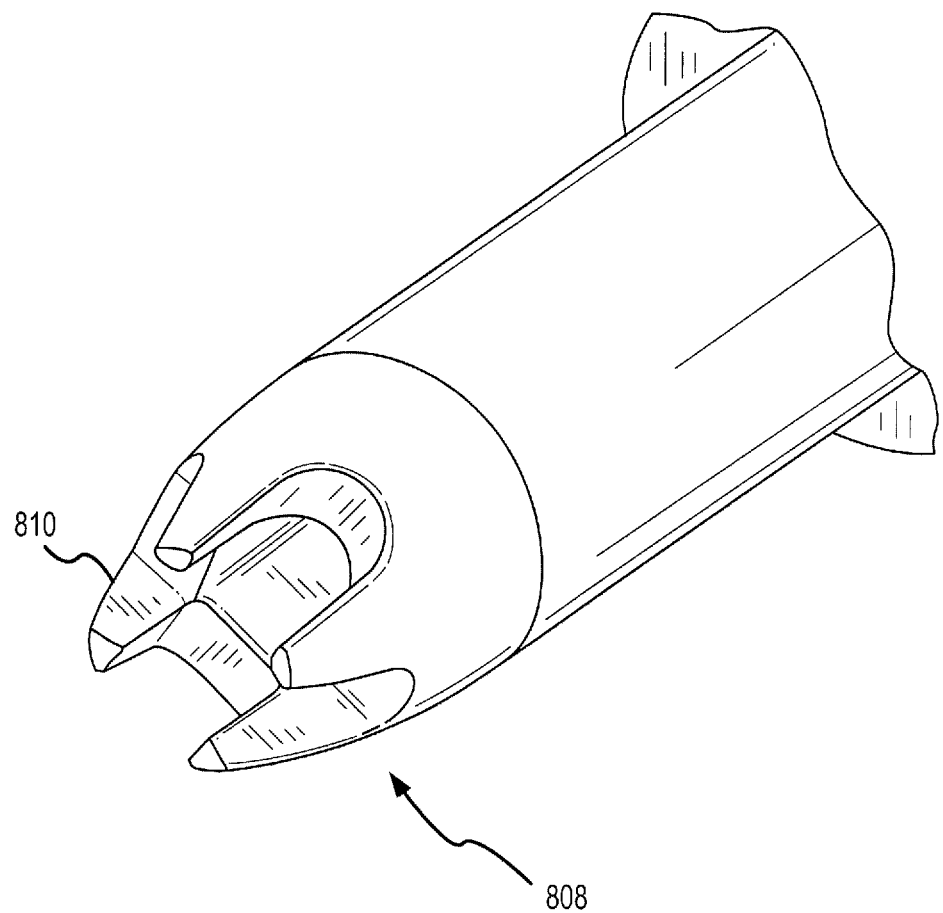
FIG. 8 illustrates close-up perspective view of a blunt dissecting punch according to an embodiment of the present invention.

FIG. 8 illustrates a perspective view of the blunt dissecting punch illustrated in FIG. 7. The blunt dissecting punch 808 includes a tapered portion and is serrated to accommodate removal of the follicular unit from the surrounding skin tissue. As is illustrated in FIG. 8, the blunt dissecting punch includes 4 splines 810.

As is discussed above, the device may include a mechanism to rotate the sharp scoring punch and/or the blunt dissecting punch without the need to rotate the entire instrument, such as to move the blunt dissecting punch rapidly through the skin layers. That is, the device may include a rotation mechanism for rotating the sharp scoring punch and/or the blunt dissecting punch as they are pressed into the patient's skin.

Figure 9:
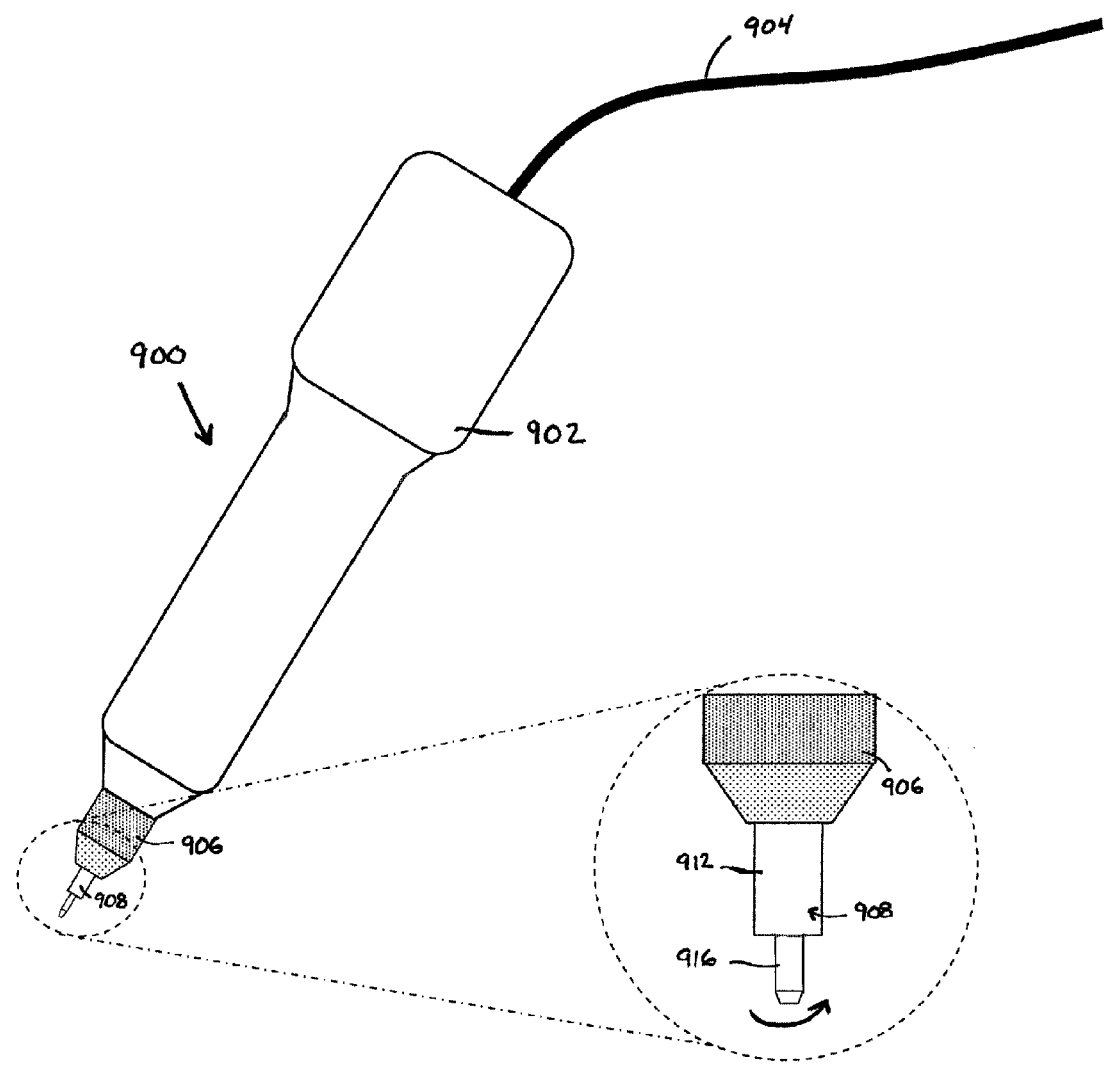
FIG. 9 illustrates a perspective view of a follicular extraction device according to an embodiment of the present invention.

In this regard, FIG. 9 illustrates a drill 900 that is adapted for the dissection of a follicular unit from a donor area of a patient so that the follicular unit may be extracted from the patient. The drill 900 includes a drill body 902 that may be adapted to be easily gripped and manipulated by an operator. The drill body 902 may also house a motor for rotating the blunt dissecting punch 908 about an elongated axis of the blunt dissecting punch 908. For example, the drill body 902 may house an electric motor that is operatively coupled to a drill chuck 906 that secures the blunt dissecting punch 908 to the drill 900. A power cord 904 may provide power to the electric motor and may also provide signals to the electric motor, such as from a control unit 930 (FIG. 11) to control, for example, the rotational speed and/or torque of the rotating dissecting punch 908. However, it will be appreciated that a power supply may also be self-contained within the drill body 902, such as by using primary or rechargeable batteries, for example. Further, a portion of the rotation mechanism may be located wholly or partially separate from the drill body 902, such as where the dissecting punch 908 is rotated using an external motor that is operatively connected to the drill 900 through a drive belt to rotate the dissecting punch 908.

The blunt dissecting punch 908 is disposed at a distal end of the drill body 902 and may be generally aligned with a longitudinal axis of the drill body 902 to enable an operator to easily grip the drill body 902 and align the dissecting punch 908 over a follicular unit. As is noted above, the blunt dissecting punch 908 may be removably attached to the drill 900 using a chuck 906 or similar clamping mechanism that is adapted to securely retain the blunt dissecting punch 908. In this manner, the dissecting punch 908 may be easily removed from the drill 900 and replaced when needed. In this regard, the dissecting punch 908 may be autoclavable for re-use of the dissecting punch 908.

During the dissection of a follicular unit from the donor area of a patient, it may be desirable to rotate the dissecting punch 908 at a first rotational speed that is sufficiently high to score the epidermis layer of the skin, and then at a second rotational speed that is lower than the first rotational speed, to dissect (separate) the follicular unit from the surrounding fatty tissue while decreasing the probability of transecting a follicular unit with the dissecting punch 908. In this regard, the drill 900 may be adapted to rotate the dissecting punch 908 at two or more rotational speeds, such as over a range of rotational speeds. For example, the drill 900 may be adapted to rotate the dissecting punch 908 at a first rotational speed of at least about 3000 rpm, such as at least about 3500 rpm, or at least about 4500 rpm. Such speeds will generally be sufficient to enable the dissecting edge 918 (FIG. 10) of the dissection punch 908 to score the epidermis layer of the skin without undue pressure being applied to the dissecting punch 908.

The rotational speed of the dissecting punch 908 may then be lowered to a second rotational speed as the dissecting punch moves through the dermis layer and the fatty tissue layer of the skin. The second rotational speed may be selected to be low enough such that the probability of transecting a follicular unit is low, while being high enough that the dissecting punch 908 can move through the fatty tissue layer without undue pressure being applied. In this regard, the second rotational speed may be much lower than the first rotational speed. In one aspect, the second rotational speed is not greater than 70 percent of the first rotational speed, such as not greater than 60 percent of the first rotational speed or even not greater than 50 percent of the first rotational speed. For example, the second rotational speed may be not greater than about 3000 rpm, such as not greater than about 2000 rpm, not greater than about 1500 rpm, not greater than about 1000 rpm, or even not greater than 500 rpm. Lower rotational speeds may be advantageous to reduce the probability of transection of a follicular unit. However, the rotational speed should be sufficiently high to maintain the ability to move the dissection punch through the fatty tissue layer. For example, the second rotational speed may be at least about 100 rpm, such as at least about 200 rpm, although lower rotational speeds may also be sufficient.

The rotational speed of the dissecting punch 908 may be adjusted manually by an operator or may be adjusted in a self-regulated manner, such as by controlling the torque of the rotating dissecting punch 908. A high torque will tend to maintain a constant or near-constant rotational speed as the dissecting punch 908 is moved through the dermis layer and into the fatty tissue layer of the skin. However, the application of a relatively low torque may advantageously enable the rotational speed of the dissecting punch 908 to self-regulate and to lower as the dissecting punch 908 moves through the skin layers. That is, at a sufficiently low torque, the friction between the blunt dissecting punch 908 and the surrounding skin layers may cause the rotational speed to lower from a first rotational speed that is initially encountered when the dissecting punch 908 first contacts the skin to a desired lower second rotational speed as the dissecting punch 908 moves through the dermis layer and the fatty tissue layer. In this regard, the torque applied to the dissecting punch 908 by the drill 900 may be not greater than about 0.04 N·m, such as not greater than about 0.03 N·m. To ensure the ability of the dissecting punch 908 to score the epidermis layer, the torque may be at least about 0.01 N·m. The rotational speed may decrease gradually as the dissecting punch 908 is moved through the skin layers, or may decrease in a step-wise fashion, such as when the torque and/or rotational speed are manually adjusted.

Figure 10:
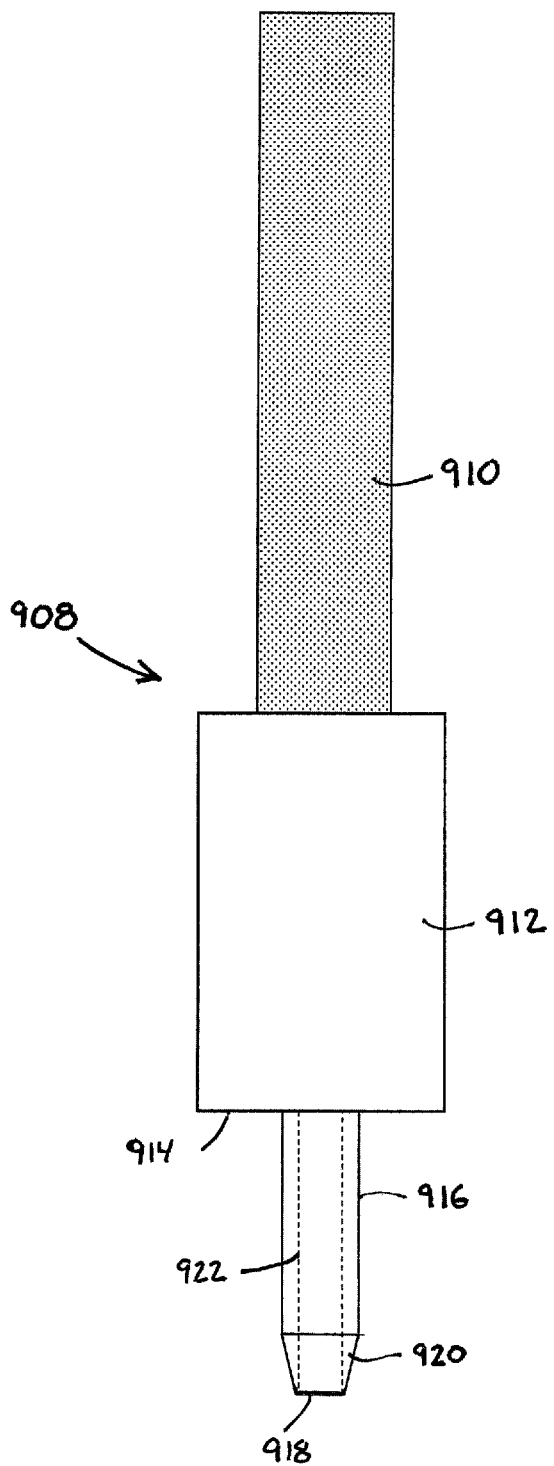
FIG. 10 illustrates a perspective view of a dissection punch according to an embodiment of the present invention.
Figure 11:
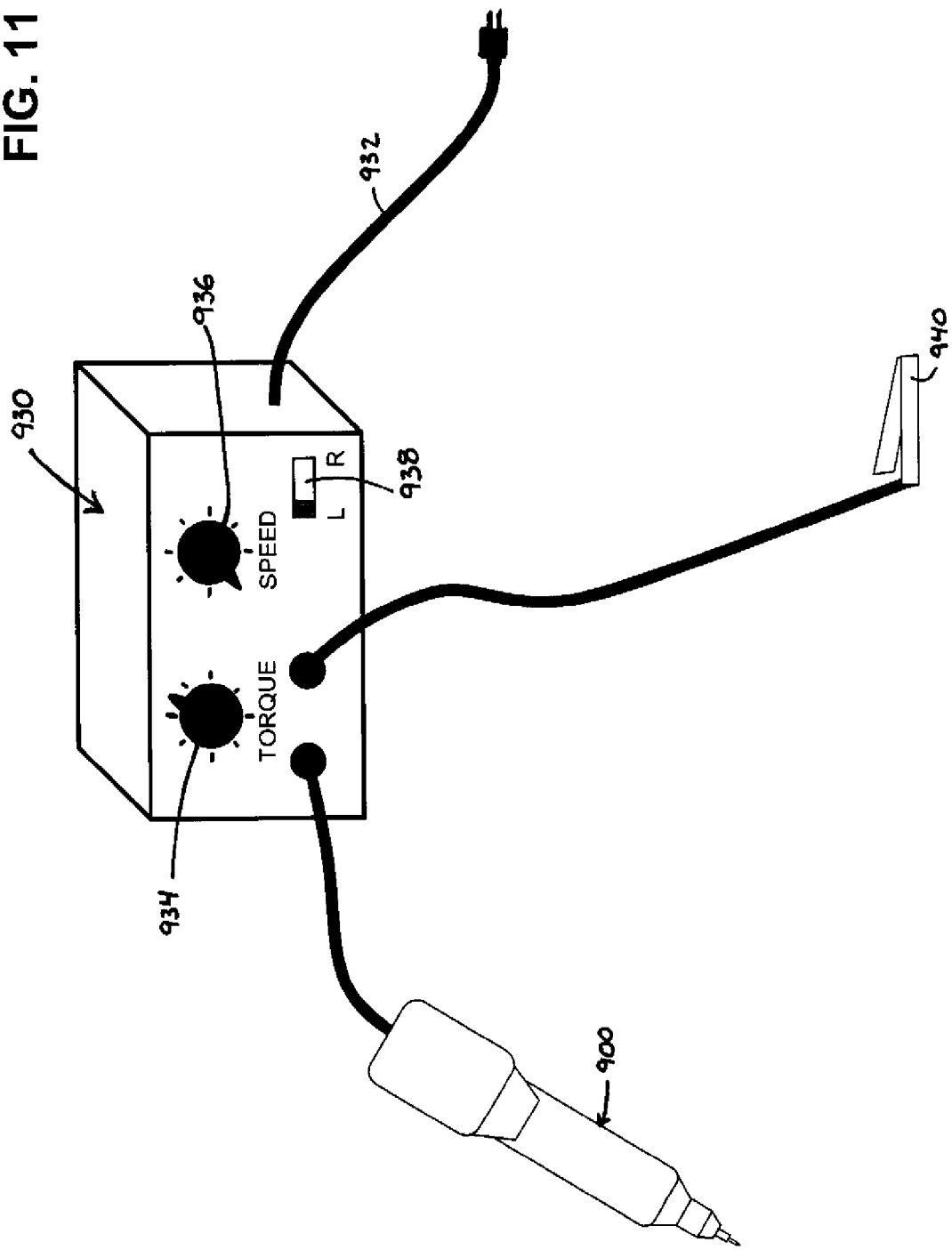
FIG. 11 illustrates an apparatus including a follicular extraction device according to an embodiment of the present invention.

The blunt dissecting punch may have a configuration and shape substantially as illustrated in FIGS. 6-8. For example, the dissecting edge of the blunt dissecting punch may be serrated. As illustrated in FIGS. 9-11, and particularly as illustrated in detail in FIG. 10, the blunt dissecting punch 908 includes a gripping shaft 910 that is adapted to be inserted into a chuck 906 (FIG. 9) or similar clamping device to secure the blunt dissecting punch 908 to the drill 900. A central portion 912 of the dissecting punch has a diameter that is larger than the diameter of the gripping shaft 910 to enable control the depth of insertion of the dissecting punch 908 into the chuck. A dissecting tip 916 extends downwardly from the central portion 912. The dissecting tip 916 has a smaller outer diameter than the central portion 912, thereby forming a shoulder 914 above the dissecting tip 916. The shoulder 914 may serve as a depth-limiting mechanism, limiting the depth of insertion of the dissecting punch 908 to the length of the dissecting tip 916. In this regard, the dissecting tip 916 may have a length of not greater than about 5 mm, for example.

The dissecting tip 916 may also include a tapered portion 920 that is tapered inwardly toward the dissecting edge 918 to ease the insertion of the dissecting punch 908 into the skin. The tapered portion may have a configuration that is similar to the tapered portion of the punch illustrated in FIG. 6. The dissecting edge 918 is located at a distal end of a lumen 922, and may be substantially circular. The dissecting edge 918 may have an inner diameter that is sufficiently large to surround a singular follicular unit, but without impinging upon adjacent follicular units. For example, the circular dissecting edge 918 may have an inner diameter of at least about 0.1 mm, such as at least about 0.7 mm, and may be not greater than about 1.1 mm.

The lumen 922 is disposed along an elongated axis of the dissecting punch and is adapted to wholly or partially receive a follicular unit therein during dissection. The lumen 922 may have a length of at least about 5 mm or at least about 8 mm, for example. The dissecting punch 908 is preferably fabricated from an autoclavable material, such as tool steel or stainless steel.

FIG. 11 illustrates an apparatus that may be useful for the dissection of follicular units from a patient in the manner described above. The apparatus includes a drill 900 that is operatively connected to a control unit 930. The drill 900 may be substantially as described above with respect to FIG. 9. The control unit 930 may provide controlled AC or DC power to the drill 900 when power cord 932 is connected to a power source. The control unit 930 may also enable control of the torque and/or the rotational speed of the dissecting punch that is affixed to the drill 900. For example, the control unit 930 may include torque control 934 and/or speed control 936 that may be manually adjusted by the operator. A switch 938 may also be provided to manually change the rotational direction of the dissecting punch. A foot control 940 may also be provided to enable an operator to activate and deactivate the drill 900 without the use of the operator's hands. The foot pedal 940 may also provide a means to adjust the rotational speed or torque of the dissecting punch by pressing and depressing the foot pedal 940, as desired.

The control unit 930 may also include means to detect the rotational speed and/or torque of the dissecting punch and make adjustments as desired during the follicular extraction procedure. For example, the control unit 930 may be capable of detecting the resistance to rotation of the dissecting punch, and adjust the rotational speed as desired.

Using the method and device described with respect to FIGS. 9-11, follicular extraction rates in excess of 600 per hour or higher may be achieved, with transection rates of less than 10% or lower.

Further, although illustrated as a hand-held device, the drill may be mounted on an arm that is manipulated manually or by computer control. For example, the drill may be mounted on a support arm to be manipulated manually by an operator to reduce fatigue on the operator's arm during a procedure. The drill may also be manipulated using, for example, computer-controlled robotics to align the dissecting punch with follicular units and dissect the follicular units.

EXAMPLES

The method of the present invention is carried out to perform follicular extraction on a number of patients. Testing includes patients with demanding hair types, African Americans and those with gray hair, and the results are substantially zero transaction on a limited number of samples. Extrapolation of timing trials using the method of the present invention reveals the ability to extract 300 to 400 grafts per hour. This rate of graft production may convey the ability to transplant up to 2000 grafts per day. A device combining multiple components has the potential to double this graft production rate and allow cases of up to 3000 grafts per day.

The serrated dissecting punch according to the present invention can reduce the frequency of buried follicular units, a phenomenon where the dissecting punch pushes the follicular unit into the skin tissue. In another example, three patients are enrolled in a follicular extraction procedure, receiving a total of 422 grafts. The method of the present invention is utilized wherein a sharp dissection of the epidermis is made with a 1 mm punch (Miltex, Inc., Bethpage, N.Y.) to a depth of about 1.3 mm followed by the insertion of a blunt serrated dissecting punch (similar to that illustrated in FIG. 8) to a depth of 5 mm. The follicular units are then removed with Foerster forceps. Follicular transaction rates and the incidents of buried follicular units are recorded.

The grafts represent a possible total of 1207 follicles, with 48 follicles transected. This is a follicular transaction rate of 4 percent. In this series of 422 extracted grafts, there are 4 buried grafts with 3 retrieved, representing a graft burial rate of 0.9% and a non-retrieval rate of 0.2%. The serrated tip allows for a more rapid and smoother insertion process that enhances the dissection process.

In another example, a drill and dissecting punch similar to that illustrated in FIGS. 9-11 is used to perform follicular extraction on a number of patients. Follicular extractions are performed at a rate of between 400 and 700 per hour, with an average of about 600 per hour. Even at this high extraction speed, the average transection rate is less than 9 percent.

While various embodiments of the present invention have been described in detail, it is apparent that modifications and adaptations of those embodiments will occur to those skilled in the art. However, it is to be expressly understood that such modifications and adaptations are within the spirit and scope of the present invention.

What is claimed is:

1. A method, for the extraction of a follicular unit from a donor area, comprising the steps of:
   aligning a blunt dissecting punch over a follicular unit in a donor area, the blunt dissecting punch comprising a lumen along its elongated axis and a dissecting edge disposed at a distal end of the lumen;
   mechanically rotating the blunt dissecting punch at a first rotational speed;
   scoring the epidermis layer of the skin with the rotating blunt dissecting punch, whereby one or more hair follicles of a follicular unit are at least partially disposed within the lumen;
   moving the rotating blunt dissecting punch through the dermis layer and into the fatty tissue layer of the skin, whereby at least a portion of the follicular unit is disposed within the lumen, to bluntly dissect the follicular unit from tissue surrounding the follicular unit; and
   extracting the follicular unit from the donor area,
   wherein the step of rotating the blunt dissecting punch comprises rotating the blunt dissecting punch at a torque that is sufficiently low such that the friction between the blunt dissecting punch and the skin layers causes the rotational speed of the blunt dissecting punch to decrease to a second rotational speed, which is not greater than about 60% of the first rotational speed.

2. A method as recited in claim 1, wherein the dissecting edge is substantially circular.

3. A method as recited in claim 2, wherein the circular dissecting edge has an inner diameter of at least about 0.1 mm and not greater than about 1.1 mm.

4. A method as recited in claim 2, wherein the circular dissecting edge has an inner diameter of at least about 0.7 mm and not greater than about 1.1 mm.

5. A method as recited in claim 1, wherein the blunt dissecting punch is moved through a total skin depth of at least about 1.5 mm and not greater than about 8 mm.

6. A method as recited in claim 1, wherein the blunt dissecting punch is moved through a total skin depth of at least about 4 mm and not greater than about 7 mm.

7. A method as recited in claim 1, wherein the step of extracting the follicular unit from the donor area comprises pulling the follicular unit from the donor area.

8. A method as recited in claim 7, wherein the step of extractinq the follicular unit comprises pulling the follicular unit from the donor area using forceps.

9. A method as recited in claim 1, wherein the first rotational speed is at least about 3000 rpm.

10. A method as recited in claim 1, wherein the first rotational speed is at least about 3500 rpm.

11. A method as recited in claim 1, wherein the second rotational speed is not greater than about 2000 rpm.

12. A method as recited in claim 1, wherein the second rotational speed is not greater than about 1500 rpm.

13. A method as recited in claim 1, wherein the second rotational speed is not greater than about 50% of the first rotational speed.

14. A method as recited in claim 1, wherein the torque is not greater than about 0.03 N·m.

15. A method for the extraction of a follicular unit from a donor area, comprising the steps of:
   aligning a blunt dissecting punch over a follicular unit in a donor area, the blunt dissecting punch comprising a lumen along its elongated axis and a circular blunt dissecting edge disposed at a distal end of the lumen, the circular blunt dissecting edge having an inner diameter of at least about 0.7 mm and not greater than about 1.1 mm;
   mechanically rotating the blunt dissecting punch at a first rotational speed that is at least about 2500 rpm;
   scoring the epidermis layer of the skin with the rotating blunt dissecting punch, whereby one or more hair follicles of a follicular unit are at least partially disposed within the axially disposed lumen;
   moving the rotating blunt dissecting punch through the dermis layer and into the fatty tissue layer of the skin, whereby at least a portion of the follicular unit is disposed within the lumen to bluntly dissect the follicular unit from tissue surrounding the follicular unit, and wherein the rotational speed of the blunt dissecting punch is decreased to a second rotational speed that is not greater than about 70% of the first rotational speed when the blunt dissecting punch is moved through the dermis layer and into the fatty tissue layer; and
   extracting the follicular unit from the donor area wherein the step of rotating the blunt dissecting punch comprises rotating the blunt dissecting punch at a torque that is sufficiently low such that the friction between the blunt dissecting punch and the skin layers causes the rotational speed of the blunt dissecting punch to decrease to the second rotational speed when the blunt dissecting punch is moved through the dermis layer and into the fatty tissue layer.

16. A method as recited in claim 15, wherein the second rotational speed is not greater than about 1000 rpm.

17. A method as recited in claim 15, wherein the torque is not greater than about 0.04Nm.

* * * * *